United States Patent

Kubo et al.

[11] 3,972,909
[45] Aug. 3, 1976

[54] α,α-DIMETHYLBENZYLUREAS AND USE AS HERBICIDES

[75] Inventors: Hiroshi Kubo, Yokohama; Tatuya Michibayashi, Kawasaki; Nansho Seki, Tokyo; Noriyuki Sato, Yokohama, all of Japan

[73] Assignee: Shova Denko Kabushiki Kaisha, Tokyo, Japan

[22] Filed: Oct. 29, 1974

[21] Appl. No.: 518,812

[30] Foreign Application Priority Data
   Oct. 30, 1973  Japan.................. 48-121204

[52] U.S. Cl................. 260/453 R; 71/120
[51] Int. Cl.$^2$........................ C07C 119/20
[58] Field of Search............ 260/453 R; 71/120

[56] References Cited
UNITED STATES PATENTS

| | | | |
|---|---|---|---|
| 3,306,726 | 2/1967 | Berliner et al. | 260/453 R |
| 3,388,153 | 6/1968 | Johnson | 260/453 R |
| 3,388,158 | 6/1968 | Surrey | 71/120 |
| 3,483,296 | 12/1969 | Martin et al. | 71/120 |
| 3,681,422 | 8/1972 | Scherer | 260/453 R |
| 3,799,964 | 3/1974 | van Daalen et al. | 71/120 |

OTHER PUBLICATIONS
Lambert et al., "Aliphatic Nitro Compds. XIX, etc.," (1949), CA43, pp. 6993–6994, (1949).

*Primary Examiner*—Glennon H. Hollrah
*Attorney, Agent, or Firm*—Sherman & Shalloway

[57] ABSTRACT

A compound of the formula

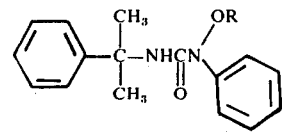

wherein R represents a member selected from alkyl and alkenyl radicals of at most 4 carbon atoms,
and a method for controlling weed growth which comprises applying to the locus to be treated a herbicidally effective amount of said α, α-dimethylbenzylurea compound.

6 Claims, No Drawings

α,α-DIMETHYLBENZYLUREAS AND USE AS HERBICIDES

This invention relates to N-alkoxy-(or N-alkenyloxy-)-N'-(α,α-dimethylbenzyl)-N-phenylureas, a herbicidal composition containing the compound as an active ingredient, and a method for controlling weed growth employing the composition.

More particularly, this invention is directed to novel compounds of Formula I

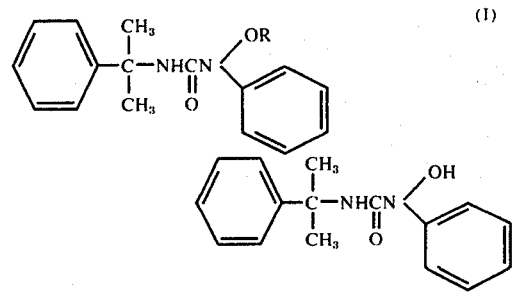

wherein R is an alkyl or alkenyl radical of at most 4 carbon atoms.

UTILITY

The α,α-dimethylbenzylureas of Formula I represent a new class of potent herbicides, and suppress both sprouting of weed seeds and growing of weed seedlings. These compounds are useful for general weed control. By properly selecting the rate or time of application of the compound of the invention, weeds growing in crop fields can be controlled selectively.

These compounds can control such germinating grass weeds as crabgrass (*Digitaria* sp.), bluegrass (*Poa* sp.), foxtail (*Alopecurus* sp.), barnyard grass (*Echinochloa* sp.), or green foxtail (*Setaria* sp.), and such broadleaf weeds as lambsquaters (*Chenopodium* sp.), pigweed (*Amaranthus* sp.), or chickweed (*Stellaria* sp.). Especially these compounds are unique in that they exert their action against such perennial weeds as nutsedge (*Cyperus* sp.), sedge (*Carex* sp.), or spikerus (*Eleocharis* sp.), which have previously been difficult to control.

Certain cultivated crops are essentially tolerant of these compounds of the invention. For example, peanuts, turf, rice, or cotton are quite tolerant of these compounds. Thus these new herbicides are especially useful for selective control of weeds in the crop fields.

PREPARATION OF COMPOUNDS

The active compounds of Formula I may be obtained by the following reaction:

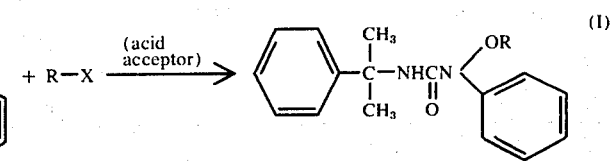

In this reaction scheme, R is as defined for Formula I and X represents a halogen atom.

The compounds of the invention are liquid or solid and are hardly soluble in cold water, but are easily soluble in most of common organic solvents. The chemical structure of the compounds are determined by means of elementary analysis, nmr spectral analysis, and mass spectral analysis.

Typical examples of the compounds of this invention are shown in Table 1. The compounds exemplified in the table are representatively abbreviated by a series of coding numbers. Hereinbelow, the compounds will be identified by these coding numbers.

In Table 1, melting points were taken on a Koffler hot-bench, nmr spectra were obtained using a 100-MHz Hitachi spectrometer in CDCl$_3$ with TMS as an internal standard; and symbols of $s$, $d$, $t$, $q$, $m$, and $J$ stand for singlet, doublet, triplet, quartet, multiplet, and coupling constant, respectively.

Table I

| Coding number | Chemical structure | Physical contant | | nmr δ-Value 100-MHz in CDCl$_3$ |
|---|---|---|---|---|
| | | Melting point (°C) | Refractive ($n_D^{26}$) | |
| 1 | R=CH$_3$ | 75.2 | — | 1.73 (6H,s), 3.72 (3H,s), 6.38(1H, br.s). 7.10~7.55 (10H,m) |
| 2 | R=C$_2$H$_5$ | 48.5 | — | 1.30 (3H, t, J=7Hz), 1.73(6H,s), 3.95(2H, q, J=7Hz), 6.40(1H, br.s), 7.10~7.55 (10H,m) |
| 3 | R=C$_3$H$_7$-n | — | 1.5537 | 0.90 (3H,6, J=7Hz), 1.60(2H,m), 1.68(6H, s), 3.77(2H, 6, J=7Hz), 6.41(1H. br.s) 7.0~7.55(10H, m) |
| 4 | R=CH$_2$CH=CH$_2$ | — | 1.5611 | 1.71(6H,s), 4.34 |

Table 1-continued

| Coding number | Chemical structure | Physical constant | | nmr δ-Value 100-MHz in CDCl₃ |
|---|---|---|---|---|
| | | Melting point (°C) | Refractive ($n_D^{26}$) | |

Structure: phenyl-C(CH₃)(CH₃)-NHC(=O)N(OR)(phenyl-CH₂—)

| 5 | R=C₄H₉-n | — | 1.5469 | (2H, d, J=7Hz), 5.32 (1H, d, J=11Hz), 5.34 (1H, d, J=16Hz), 6.10 (1H, m), 6.40 (1H, br,s), 7.0–7.5 (10H, m) 0.90 (3H, t, J=7Hz), 1.50 (4H, m), 1.71 (6H, s), 3.86(3H, t, J=6Hz), 6.41 (1H, br.s), 7.0–7.5 (10H, m) |

The following specific example illustrates the method of preparation.

N-Methoxy-N'-(α,α-dimethylbenzyl)-N-phenylurea (Compound 1)

To a sodium alcoholate solution prepared from 1.0 gram (0.044 mole) of sodium in 40 ml of absolute methanol were added 10.8 grams (0.04 mole) of N-hydroxy-N'-(α,α-dimethylbenzyl)-N-phenylurea, and the mixture stirred until the solid dissolved. To this solution were added 6.5 grams (0.046 mole) of methyl iodide, and the mixture kept at 40°–50°C for 4 hours. The reaction mixture was concentrated under reduced pressure and the residue was extracted with hot benzene. The extract was concentrated and the residue was recrystallized to obtain 10.4 grams of compound 1, which melts at 75.2°C.

HERBICIDAL FORMULATIONS

The following examples, in which the parts are by weight, are given primarily by way of illustration.

EXAMPLE 1

Wettable powder

A wettable powder containing 50% of the active ingredient is prepared by blending 50 parts of compound 1, 2, 3, 4, or 5, 45 parts of bentonite, and 5 parts of polyoxyethylenealkylaryl ether. Prior to application, the wettable powder is diluted with water to a suitable concentration to obtain a homogeneous suspension of the herbicide.

EXAMPLE 2

Emulsifiable concentrate

A emulsifiable concentrate containing 50% of the active ingredient is prepared by blending 50 parts of compound 1, 2, 3, 4, or 5, 42 parts of xylene, and 8 parts of a nonionic surfactant. The emulsifiable concentrate is diluted with water to a suitable concentration just before application.

EXAMPLE 3

Granules

Ten parts of compound 1, 2, 3, 4, or 5 in Table 1 are blended with 15 parts of bentonite, 73 parts of clay, and 2 parts of sodium dodecylbenzenesulfonate. The blend was then moistened with about 25 parts of water, and extruded through die holes. The extrudate is dried and cut to obtain granules containing 10% of the active ingredient.

The herbicidal composition containing the compound of this invention as an effective ingredient, as illustrated by the above examples, can be prepared in various formulations such as a wettable powder, emulsifiable concentrate, granule or dust. Examples of inert agricultural and horticultural diluents used to prepare these formulations include water, organic solvents such as benzene, toluene, xylene, kerosene, ketones, dimethyl formamide or Freons, and solid fillers such as clay, talc, bentonite, diatomaceous earth, starch or kaolin. The wettable powders and emulsifiable concentrates are marketed as formulations containing about 10 to 80% by weight, usually about 50% by weight, of the compounds of this invention, and are diluted optionally with water prior to use. The minimum concentration of the compound in these formulations can be about 0.1% by weight. On the other hand, granules and dusts are marketed as formulations containing the compounds of this invention in a concentration of about 5 to 80% by weight, and prior to use, a solid filler is added as required, and they are applied as formulations containing about 5 to 10% by weight of the compound of this invention.

In order to control weed growth, the herbicidal composition of this invention is applied so that about 0.5 to 10 Kg, usually about 1 to 5 Kg, of the compound of this invention is distributed per hectare of the locus to be treated.

HERBICIDAL PROPERTIES

In order to illustrate the specific herbicidal activity and surprising selectivity of the compounds of the present invention, a series of test results are shown below.

Test 1

Herbicidal test in paddy rice field

Ceramic pots of 1/500000 hectare in size were packed with paddy soil. Seeds of barnyard grass (*Echinochloa Crusgalli*) and two sorts of typical broadleaf weeds were sown on the surface of soil. Then two sheaves of slender spikerush (*Eleocharis acicularis*) were transplanted into each pot, and watered to the depth of 3 cm to provide paddy conditions. Two sheaves of rice seedlings were transplanted into each pot the next day. After three days, a wettable powder of each of the compounds of this invention, prepared after Example 1, was diluted with water, and used to treat the irrigation water at the dosage of 10, 5, and 2.5 kg per hectare. Herbicidal effects and phytotoxicity to the test plants were observed after three weeks. Diuron and linuron were used as reference herbicides. Phytotoxic ratings range from 0 to 5 with 0 meaning no phytotoxicity and 5 indicating a complete kill of the plant:

5= Complete kill
4= 80 — 99% Damage
3= 60 — 79% Damage
2= 40 — 59% Damage
1= 20 — 39% Damage
0= 0 — 19% Damage The results of the tests are summarized in Table 2.

The results given in Table 2 demonstrate that the compounds of this invention possess strongly herbicidal activity against barnyard grass, slender spikerush, and broadleaf weeds. Furthermore it is clear that these compounds are selective to the rice plant.

TABLE 2

Herbicidal effect in paddy rice field

| Compound tested | Active ingredient (kg/hectare) | Barnyard grass | Slender spikerush | Broad-leaf weeds | Rice |
|---|---|---|---|---|---|
| 1 | 10 | 5 | 5 | 5 | 1 |
|   | 5 | 5 | 5 | 5 | 1 |
|   | 2.5 | 5 | 5 | 5 | 0 |
| 2 | 10 | 5 | 5 | 5 | 1 |
|   | 5 | 5 | 5 | 5 | 0 |
|   | 2.5 | 5 | 4 | 4 | 0 |
|   | 10 | 5 | 5 | 5 | 0 |
| 3 | 5 | 5 | 4 | 4 | 0 |
|   | 2.5 | 5 | 4 | 4 | 0 |
|   | 10 | 5 | 5 | 5 | 0 |
| 4 | 5 | 5 | 5 | 5 | 0 |
|   | 2.5 | 5 | 4 | 4 | 0 |
|   | 10 | 5 | 5 | 4 | 0 |
| 5 | 5 | 4 | 4 | 4 | 0 |
|   | 2.5 | 3 | 3 | 3 | 0 |
| Diuron (Reference herbicide) | 10 | 5 | 2 | 5 | 5 |
|   | 5 | 5 | 1 | 5 | 4 |
|   | 2.5 | 5 | 1 | 4 | 4 |
| Linuron (Reference herbicide) | 10 | 5 | 1 | 5 | 5 |
|   | 5 | 5 | 0 | 5 | 3 |
|   | 2.5 | 5 | 0 | 4 | 2 |
| Untreated | — | 0 | 0 | 0 | 0 |

Test 2

Pre-emergence soil treatment test

Ceramic pots were packed with soil. Seeds of rice, corn, peanut, and cotton were sown onto the surface, and covered with soil containing seeds of crabgrass (*Digitaria sp.*), barnyard grass (*Echinochloa Crusgalli*), green foxtail (*Setaria sp.*), and lambsquaters (*Chenopodium sp.*) by 2 cm in thickness. On the next day, a wettable powder of each of the compounds of this invention, prepared after Example 1, was diluted with water, and sprayed on the surface of soil at the dosage of 10, and 5 kg per hectare. Herbicidal effects were assessed after four weeks. Phytotoxic ratings were given on the same scale as in Test 1. Diuron and linuron were used as reference herbicides.

The results of the tests are summarized in Table 3. These results show that the compounds of this invention are strongly herbicidal against a broad range of upland weeds. These compounds are tolerant to peanut and cotton, so that they can be used as selective herbicides in a peanut or cotton fields.

Table 3

Pre-emergence soil treatment test

| Compound tested | Dosage (kg/ha) | Crab grass | Barnyard grass | Green foxtail | Lambs-quaters | Rice | Corn | peanut | Cotton |
|---|---|---|---|---|---|---|---|---|---|
| 1 | 10 | 5 | 5 | 5 | 5 | 3 | 3 | 1 | 2 |
|   | 5 | 5 | 5 | 5 | 4 | 2 | 2 | 0 | 1 |
| 2 | 10 | 5 | 5 | 5 | 5 | 3 | 3 | 0 | 1 |
|   | 5 | 5 | 5 | 5 | 3 | 2 | 2 | 0 | 0 |
| 3 | 10 | 5 | 5 | 5 | 5 | 2 | 2 | 0 | 0 |
|   | 5 | 4 | 4 | 3 | 2 | 1 | 1 | 0 | 0 |
| 4 | 10 | 5 | 5 | 5 | 5 | 2 | 3 | 1 | 2 |
|   | 5 | 5 | 5 | 5 | 4 | 1 | 2 | 0 | 1 |
| 5 | 10 | 5 | 5 | 5 | 5 | 2 | 3 | 0 | 2 |
|   | 5 | 5 | 4 | 5 | 5 | 1 | 2 | 0 | 1 |
| Diuron (Reference herbicide) | 10 | 5 | 5 | 5 | 5 | 5 | 4 | 5 | 2 |
|   | 5 | 5 | 4 | 5 | 4 | 5 | 2 | 2 | 1 |
| Linuron (Reference herbicide) | 10 | 5 | 5 | 5 | 5 | 5 | 3 | 5 | 2 |
|   | 5 | 5 | 4 | 5 | 4 | 4 | 1 | 2 | 1 |
| Untreated | — | 0 | 0 | 0 | 0 | 0 | 0 | 0 | 0 |

Test 3

Test for nutsedge control

Ceramic pots were packed with soil. Ten tubers of purple nutsedge (*Cyperus rotundus*) were planted 5 cm deep in each pot. Three days later, a wettable powder of each of the compounds of this invention, prepared after Example 1, was diluted with water, and sprayed on the surface of the pot at the dosage of 10, 5, and 2.5 kg per hectare. Herbicidal activity was evaluated after forty days, and phytotoxic ratings were given on the same scale as in Test 1.

The results of the tests are summarized in Table 4. The compounds of this invention are specifically effective in controlling purple nutsedge, which has previously been difficult to eradicate.

Table 4

Tests for purple nutsedge control

| Dosage (kg/hectare) | Compounds tested 1 | 2 | 3 | 4 | Diuron (Reference herbicide) | Untreated |
|---|---|---|---|---|---|---|
| 10 | 5 | 5 | 4 | 5 | 2 | 0 |
| 5 | 5 | 5 | 4 | 5 | 1 | 0 |
| 2.5 | 5 | 5 | 3 | 4 | 0 | 0 |

Test 4

Test for annual bluegrass control in turf

Ceramic pots of 1/200000 hectare in size were packed with soil and separated into two groups. Korean turf (*Zoysia Japonica*) and tifgreen bermuda grass were trans-planted to each group. When the surface of the pot had been covered with grasses, each pot was covered with some additional top soil contaminated with seeds of annual bluegrass (*Poa annua*). Three days later, a wettable powder of each of this invention, prepared after Example 1, was diluted with water, and sprayed on the surface of soil at the dosage of 10, 5 and 2.5 kg per hectare. Herbicidal activity and phytotoxicity to the turf were evaluated after a month, and phytotoxic ratings were given on the same scale as in Test 1.

The results of tests are summarized in Table 5. The compounds of this invention are strongly herbicidal against annual bluegrass, and are tolerant to Korean turf and burmuda grass. Thus, the compounds are useful as selective herbicides in lawn.

Table 5

Tests for annual bluegrass control

| Compounds tested | Dosage (Kg/hectare) | Phytotoxicity to annual bluegrass | Phytotoxicity to Korean turf | Tifgreen |
|---|---|---|---|---|
| 1 | 10 | 5 | 0 | 1 |
|   | 5 | 5 | 0 | 0 |
|   | 2.5 | 5 | 0 | 0 |
| 2 | 10 | 5 | 0 | 1 |
|   | 5 | 5 | 0 | 0 |
|   | 2.5 | 5 | 0 | 0 |
| 3 | 10 | 5 | 0 | 0 |
|   | 5 | 5 | 0 | 0 |
|   | 2.5 | 4 | 0 | 0 |
| 4 | 10 | 5 | 0 | 1 |
|   | 5 | 5 | 0 | 0 |
|   | 2.5 | 4 | 0 | 0 |
| 5 | 10 | 5 | 0 | 0 |
|   | 5 | 4 | 0 | 0 |
|   | 2.5 | 3 | 0 | 0 |
| Diuron (Reference herbicide) | 10 | 5 | 5 | 5 |
|   | 5 | 5 | 3 | 5 |
|   | 2.5 | 5 | 2 | 3 |
| Untreated | — | 0 | 0 | 0 |

What we claim is:

1. A compound of the formula

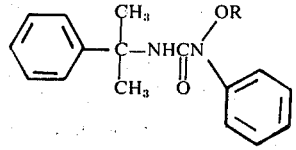

wherein R represents a member selected from alkyl and alkenyl radicals of at most 4 carbon atoms.

2. The compound of claim 1 wherein R is methyl.
3. The compound of claim 1 wherein R is ethyl.
4. The compound of claim 1 wherein R is propyl.
5. The compound of claim 1 wherein R is butyl.
6. The compound of claim 1 wherein R is allyl.

* * * * *

UNITED STATES PATENT AND TRADEMARK OFFICE
CERTIFICATE OF CORRECTION

PATENT NO. : 3,972,909
DATED : August 3, 1976
INVENTOR(S) : Hiroshi Kubo et al

It is certified that error appears in the above-identified patent and that said Letters Patent are hereby corrected as shown below:

Item 73, line 1, delete "Shova", insert -- Showa --

Signed and Sealed this

Twenty-sixth Day of October 1976

[SEAL]

Attest:

RUTH C. MASON
Attesting Officer

C. MARSHALL DANN
Commissioner of Patents and Trademarks